(12) United States Patent
Thiebaut

(10) Patent No.: US 7,470,811 B2
(45) Date of Patent: Dec. 30, 2008

(54) INTEGRATED PROCESS FOR ACETIC ACID AND METHANOL

(75) Inventor: Daniel Marcel Thiebaut, Lescar (FR)

(73) Assignee: Acetex (Cyprus) Limited, Limassol (CY)

( * ) Notice: Subject to any disclaimer, the term of this patent is extended or adjusted under 35 U.S.C. 154(b) by 0 days.

(21) Appl. No.: 10/596,955

(22) PCT Filed: Jan. 22, 2004

(86) PCT No.: PCT/CY2004/000002

§ 371 (c)(1),
(2), (4) Date: May 23, 2007

(87) PCT Pub. No.: WO2005/070855

PCT Pub. Date: Aug. 4, 2005

(65) Prior Publication Data

US 2008/0039652 A1 Feb. 14, 2008

(51) Int. Cl.
C07C 51/10 (2006.01)
C07C 51/12 (2006.01)
C07C 53/08 (2006.01)
(52) U.S. Cl. .................. 562/519; 562/517; 562/607
(58) Field of Classification Search .............. None
See application file for complete search history.

(56) References Cited

U.S. PATENT DOCUMENTS 6,781,014 B1 * 8/2004 Vidalin et al. ............ 562/607
6,846,951 B1 * 1/2005 Thiebaut .................. 562/519
7,199,276 B2 * 4/2007 Sher et al. ................ 585/640
2004/0127759 A1 * 7/2004 Van Egmond ............ 585/327
2005/0113623 A1 * 5/2005 Kuechler et al. ......... 585/639

* cited by examiner

Primary Examiner—Karl J Puttlitz
(74) Attorney, Agent, or Firm—Daniel N. Lundeen; Lundeen & Lundeen, PLLC

(57) ABSTRACT

An integrated process for making methanol, acetic acid, and a product from an associated process is disclosed. Syngas (120) is produced by combined steam reforming (109) and autothermal reforming (118) of natural gas (102) where a portion (112) of the natural gas bypasses the steam reformer (109) and is blended with the steam reformer effluent for supply to the autothermal reformer (ATR) (118) with CO2 recycle (110). A portion of the syngas is fed to CO2 removal (122) to obtain the recycle CO2 and cold box (130) to obtain a hydrogen stream (131) and a CO stream (135). The remaining syngas, hydrogen stream (131) and CO2 from an associated process are fed to methanol synthesis (140), which produces methanol and a purge stream (124) supplied to the CO2 removal unit. The methanol is supplied to an acetic acid unit (13)6 with the CO (135) to make acetic acid, which in turn is supplied to a VAM synthesis unit (148). Oxygen for both the ATR and VAM synthesis can be supplied by a common air separation unit (116), and utilities such as steam generation can further integrate the process.

25 Claims, 2 Drawing Sheets

INTEGRATED PROCESS FOR ACETIC ACID AND METHANOL

BACKGROUND OF THE INVENTION

The present invention is directed generally to an improved method for the production of, methanol, acetic acid, and other chemicals such as vinyl acetate monomer (VAM) from natural gas. The improved method integrates a carbon monoxide separation plant with a methanol synthesis unit to form an optimal syngas composition for methanol production.

Methanol is a major chemical raw material. Major uses of methanol include the production of acetic acid, formaldehyde and methyl-t-butylether. Worldwide demand for methanol is expected to grow in the next decade as new applications become commercialized such as the conversion of methanol to gas (Mobil MTG Process), the conversion of methanol to light olefins (MTO Process of UOP and Norsk Hydro), the use of methanol for power generation and the use of methanol in fuel cells. The development of such applications is clearly linked to the methanol production cost. The present invention permits the construction of highly efficient single-train plants for converting natural gas to methanol at low cost in large quantities.

The manufacture of acetic acid from carbon monoxide and methanol using a carbonylation catalyst is well known in the art. Representative references disclosing this and similar processes include U.S. Pat. Nos. 1,961,736 to Carlin et al (Tennessee Products); 3,769,329 to Paulik et al (Monsanto); 5,155,261 to Marston et al (Reilly Industries); 5,672,743 to Garland et al (BP Chemicals); 5,728,871 to Joensen et al (Haldor Topsoe); 5,773,642 to Denis et al (Acetex Chimie); 5,817,869 to Hinnenkamp et al (Quantum Chemical Corporation); 5,877,347 and 5,877,348 to Ditzel et al (BP Chemicals); 5,883,289 to Denis et al (Acetex Chimie); and 5,883,295 to Sunley et al (BP Chemicals), each of which is hereby incorporated herein by reference.

The primary raw materials for acetic acid manufacture are, of course, carbon monoxide and methanol. In the typical acetic acid plant, methanol is imported and carbon monoxide, because of difficulties associated with the transport and storage thereof, is generated in situ, usually by reforming natural gas or another hydrocarbon with steam and/or carbon dioxide. For this reason, attention has recently focused on the construction of integrated plants producing both methanol and acetic acid. A significant expense for new acetic acid production capacity is the capital cost of the equipment necessary for carbon monoxide generation. It would be extremely desirable if this capital cost could be largely eliminated or at least significantly reduced.

The primary raw materials for vinyl acetate monomer manufacture are ethylene, acetic acid and oxygen. Carbon dioxide is produced as an undesirable byproduct in the reaction and must be removed from the recycled ethylene.

A significant expense of new production capacity for syngas, methanol, acetic acid and acetic acid derivatives such as VAM, is the capital cost of the necessary equipment. Other significant expenses include the operating costs, including the cost of raw materials. It would be extremely desirable if these capital and operating costs could be reduced.

For methanol production, it is well established that for a large capacity syngas plant autothermal reforming could be the more economic process leading to synthesis gas, since large capital costs are saved by not constructing large primary reformers or multiple partial oxidation reformers. Nevertheless, the drawback is not being able to have a full usage of all carbon molecules, resulting in the venting of large quantities of $CO_2$, which is undesirable. It is in fact necessary to condition the synthesis gas at the outlet of the autothermal reformer because the stoichiometric number $(SN)=[(H2-CO2)/(CO+CO2)]$ is below 2, usually between 1.7 and 1.9. The goal is to obtain an optimum syngas ratio, which lies in the range of 2.0 to 2.1 for makeup to the methanol synthesis loop.

Lee et al discloses in U.S. Pat. No. 5,180,570 an integrated process for making methanol and ammonia in order to approach stoichiometric conditions in the methanol reaction loop. McShea, III et al disclose in U.S. Pat. No. 4,927,857 a catalyst for autothermal reforming and the means to obtain a syngas in stoichiometric proportions by controlling the steam to carbon and oxygen to carbon ratios. Supp et al disclose in U.S. Pat. No. 5,310,506 the addition of a high-hydrogen gas in the ATR feed to obtain, a synthesis gas exiting the ART suitable for methanol synthesis having a stoichiometric number of between 1.97 and 2.2. Banquy discloses in U.S. Pat. Nos. 4,888,130 and 4,999,133, a process suitable for methanol production on a very large scale where the synthesis gas can be made as close as necessary to the stoichiometric composition required for methanol production, by using the combination of both a primary steam reformer and an autothermal reactor.

In an article presented to 2000 World Methanol Conference Copenhagen Denmark Nov. 8-10, 2000, Streb shows that very large capacity methanol plants require a special process design. He suggests that pure autothermal reforming can be used when the feedstock is light natural gas, but he underlines that then the stoichiometric ratio is less than 2 and suggests the need to suppress CO2 conversion. In EP Patent Application No. 1,348,685 A1, Grobys et al disclose a process for the production of methanol wherein the syngas number is adjusted by withdrawing a carbon monoxide stream. In commonly assigned WO 03/097523A2, the present applicant discloses an integrated process that produces both methanol and acetic acid under substantially stoichiometric conditions.

In U.S. Pat. No. 6,495,609, Searle discloses the recycle of CO2 to a methanol synthesis reactor in the production of ethylene and ethylene oxide from methanol. In U.S. Pat. No. 6,444,712, Janda discloses the recycle of CO2 back to either the reformer or the methanol synthesis loops to control the SN between 1.6 and 2.1. Both Searle and Janda demonstrate the manipulation of the SN through the use of steam and partial oxidation reformers. Generally steam reformers generate syngas with an SN greater than 2.8, while partial oxidation reformers produce syngas having an SN between 1.4 and 2.1.

The rising need for hydrogen in refineries is driven by the increasingly stringent fuel specifications in terms of the content of aromatics and sulfur in gasoline and diesel. The importation of large quantities of hydrogen is necessary as hydrogen demand peaks and balances in refineries are jeopardized.

SUMMARY OF INVENTION

It has now been discovered that a combined reforming process, which uses the combination of an autothermal reformer and a classical steam reformer can be better matched for methanol production by integrating an acetic acid plant which consumes carbon monoxide for carbonylating an ad hoc stream of methanol. The hydrogen which is now freed can be advantageously used either by importing CO2 streams for example from VAM nearby plants in order to increase the methanol production, or by exporting the hydrogen surplus to a nearby refinery.

The present invention integrates a methanol synthesis process with an acetic acid process. The invention takes advantage of having a carbon monoxide separation plant upstream the methanol reactor, to adjust the remaining syngas stoichiometric number (SN) to a value between 2.0 and 2.1 and more preferably close to 2.05. The carbon monoxide is separated from a portion of the reformer effluent with CO2 recovery recycled to the reformer and hydrogen returned to the methanol synthesis. The amount of reformer effluent from which the CO is recovered is balanced to result in the desired SN for the makeup syngas to the methanol loop.

The invention provides a method that produces methanol, acetic acid and optionally vinyl acetate monomer, or the like. It also involves the discovery that the large capital costs for large scale production can be reduced through a specific manner of integrating the manufacturing processes of these compounds into one integrated process.

In one embodiment, the invention provides an integrated method for manufacturing methanol and acetic acid. The process comprises separating a hydrocarbon source into first and second hydrocarbon streams, reforming the first hydrocarbon stream with steam to produce a reformed stream, and autothermally reforming a mixture of the reformed stream and the second hydrocarbon stream with oxygen and carbon dioxide to produce a syngas stream. The process also includes separating a portion of the syngas stream into a carbon dioxide-rich stream, a hydrogen-rich stream, and a carbon monoxide-rich stream, recycling the carbon dioxide-rich stream to the autothermal reforming, and compressing a remaining portion of the syngas stream, an adequate part of the hydrogen-rich stream and a carbon dioxide stream to supply a makeup stream to a methanol synthesis loop to obtain a methanol product. The flexibility is thus given to advantageously match the SN of the makeup syngas to an optimum value of 2.05by directing any surplus of the hydrogen-rich stream from a cold box to a fuel gas system. Additionally, the SN can be adjusted by importing a CO2 stream into the methanol synthesis gas makeup stream to increase the CO2 content, or by recycling a CO2 stream upstream the autothermal reformer to increase CO produced. The CO2-rich stream can be obtained from the separation of the syngas or an associated process.

A purge gas stream from the methanol synthesis loop is preferably supplied to the separating step. The separation step preferably includes supplying the portion of the syngas stream to a methane wash cold box. Flash gas from the cold box can preferably be recycled to the methanol synthesis loop. A tail gas from the cold box can be recycled as process gas. A minor portion of a hydrogen rich stream from the cold box can be recycled to the methanol synthesis loop, and a major portion of the hydrogen rich stream can be exported for either an associated process, or to a refinery located nearby. Carbon dioxide emissions (measured as carbon dioxide mass) for the integrated complex are preferably less than 10 percent of the total carbon input (by mass), and more preferably less than 5 percent.

The process can further include synthesizing acetic acid from at least a portion of the methanol product and the carbon monoxide-rich stream. Any associated process preferably uses the acetic acid as a reactant, uses the methanol product as a reactant, shares oxygen from a common air separation unit, shares common utilities, or a combination thereof. The use of a single air separation unit, for example, significantly reduces the capital costs associated with the integrated plant. The method can also include supplying an imported carbon dioxide stream and/or a carbon dioxide stream from an associated process to the methanol synthesis loop. At least a portion of the acetic acid produced can be supplied to a vinyl acetate monomer (VAM) synthesis loop in the associated process for reaction with ethylene and oxygen to produce VAM. A CO2-rich stream from the VAM synthesis loop can be imported to the methanol synthesis loop.

The feed stream can also be pretreated by hydrogenation to allow a lower steam to carbon ratio to be employed while avoiding soot formation in the autothermal reformer, and the corresponding process facility. In this method, a hydrogen-rich stream is added to a feed gas stream containing higher hydrocarbons (2 or more carbon atoms), the resulting mixture is contacted with a hydrogenation catalyst at a hydrogenation temperature, and the hydrogenated mixture is fed to an autothermal reformer with steam and oxygen to form syngas. The hydrogen-rich stream is preferably a purge gas or fraction thereof from a methanol synthesis loop receiving syngas or a portion or fraction thereof. The hydrogen-rich stream is preferably added at a rate to provide at least a stoichiometric amount of hydrogen for hydrogenation of the higher hydrocarbons to methane. The hydrogenation temperature can preferably be from 300° C. to 550° C. The process facility in this embodiment includes a feed gas supply comprising higher hydrocarbons; a pre-hydrogenation reactor comprising hydrogenation catalyst for converting the higher hydrocarbons to form a higher-hydrocarbon-lean stream (base metals such as platinum, palladium, cobalt, molybdenum, nickel or tungsten, supported on alumina or a zeolite are commonly used as catalyst); an autothermal reformer for reacting the higher-hydrocarbon-lean stream with steam and oxygen to form a syngas stream; a methanol synthesis loop for reacting hydrogen and carbon monoxide from the syngas stream to form methanol; a purge gas stream from the methanol synthesis loop; and a line for supplying a portion of the purge gas stream to the pre-hydrogenation reactor.

Because the reaction is exothermic, the hydrogenation process can be done in one or several reactors, with intermediate coolers if it is necessary. This hydrogenation step is particularly well adapted for use with autothermal reformers having a low steam to carbon ratio in the feed.

The method can also include providing at least a portion of the acetic acid produced to a VAM synthesis loop in the associated process, and combining the portion of the acetic acid with an ethylene source and oxygen from the common air separation unit to produce VAM. Preferably, a CO2-rich stream is imported to the methanol synthesis loop from the VAM synthesis loop.

DESCRIPTION

Figure 1:
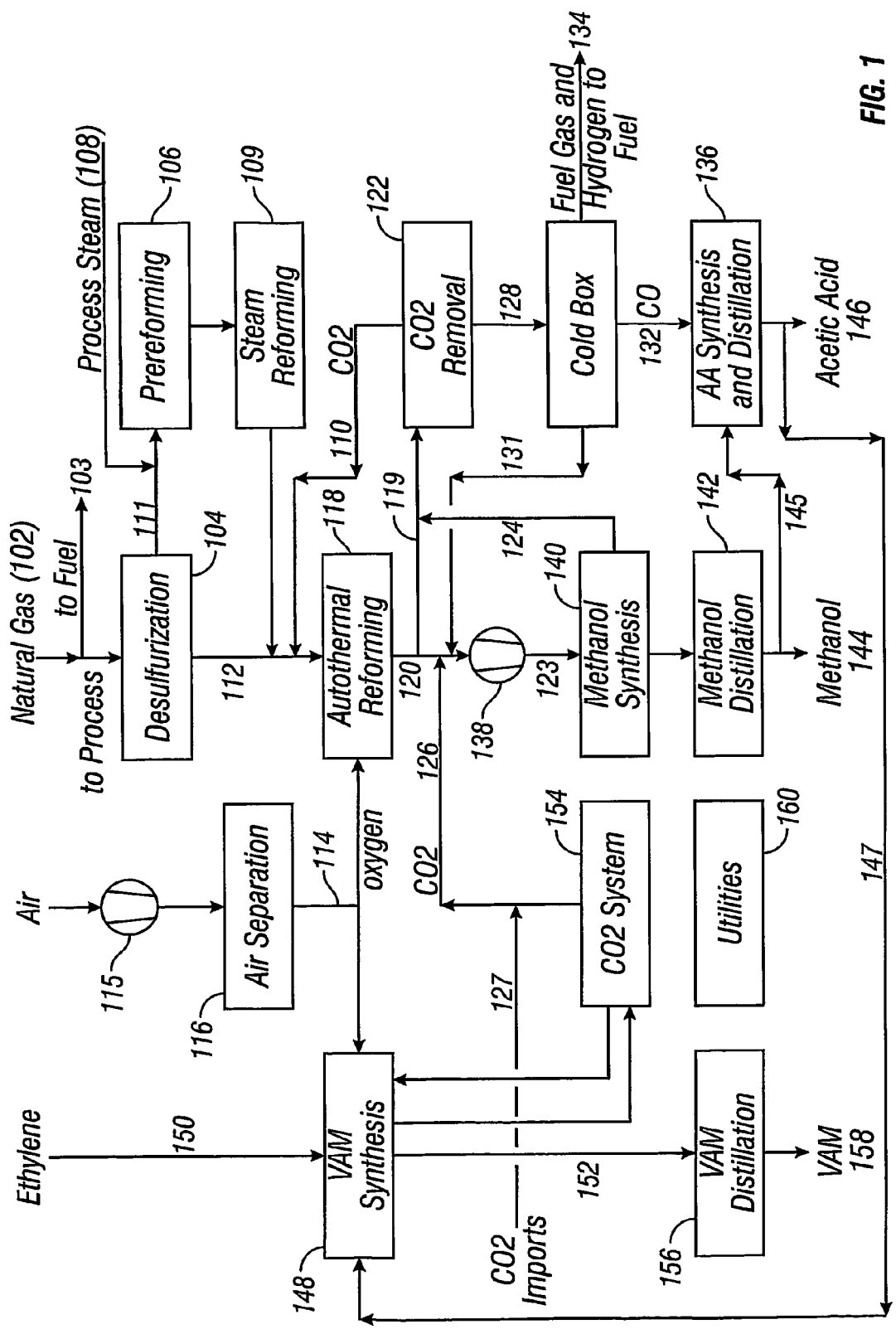
FIG. 1 is a simplified block flow diagram of an embodiment according to the present invention of a process for making methanol, acetic acid and vinyl acetate monomer, employing steam and autothermal reformers for the production of syngas.

The plant for the process can be a new plant, but it could also be a retrofit of an existing methanol, acetic acid and/or VAM plant.

Natural gas 102 is provided as both fuel 103 for the plant as well as feed gas for the synthesis. The natural gas is supplied to a conventional desulfurization unit 104 and then separated into first and second streams 111 and 112, respectively, which each comprise from 35 to 65 percent of the total natural gas in the streams 111, and 112. The first stream 111 is fed to either an adiabatic or non-adiabatic catalytic steam prereformer 106 with steam 108 before entering the conventional fired steam reformer 109. The steam reformer 109 operates at between 700 and 900° C. and between 0.7 and 3.5 MPa. The reformed effluent from the steam reformer 109 is then combined with the second stream of natural gas 112, oxygen 114 obtained from an air separation unit (ASU) 116, and a recycled CO2-rich stream 110. Air is compressed in compressor 115 and fed to ASU 116, which is operated in a conventional manner to obtain the oxygen stream 114. The mixture of natural gas, steam reformer effluent, and carbon dioxide, is introduced to autothermal reformer 118 with the oxygen for catalytic reforming using conventional autothermal reforming equipment and catalyst systems to produce syngas stream 120. The syngas stream 120 is conventionally cooled and dried.

A portion of the syngas stream 120 is fed to CO2 removal unit 122 via line 119 to produce the CO2 recycle stream 110, previously mentioned. The amount of syngas in stream 119 depends primarily on the amount of CO needed for acetic acid synthesis, but preferably comprises at least 5 percent of stream 120, more preferably at least 20 percent, up to 50 percent or more in the case where methanol export is negligible and acetic acid production is at a maximum. The methanol and acetic acid production should be matched to take full advantage of the H2, CO, and CO2 produced, preferably from 1,000 to 20,000 metric tons/day methanol and from 300 to 6,000 metric tons/day acetic acid. The more acetic acid that is produced, relative to the methanol produced, there will be more hydrogen available for reaction with the imported CO2 to maintain the SN and methanol make. If less acetic acid is produced, there will be insufficient hydrogen, e.g. the SN will be too low and the methanol make will decrease. If the total production of syngas is increased too much, the limits of the ASU can be exceeded, requiring the excessive capital cost of a second ASU, and/or the steam reformer costs increase excessively. On the other hand, if the total production is reduced too much, there is a loss of the economy of scale and the capital costs per unit of production will increase.

CO2 removal unit 122 can use conventional CO2 removal processes and equipment to remove the CO2, e.g. solvent absorption and stripping. The methanol synthesis loop purge gas stream 124, all or a portion of CO2 imported from the VAM synthesis process or another associated process, or a combination thereof, can also, if desired, be fed to the removal unit via line 119.

The CO2 removal unit produces a CO2-rich stream 110 and a mixed CO/H2 stream 128 essentially free of CO2. The CO2-rich stream 110 is introduced to the syngas stream 112 upstream the autothermal reformer 118.

Separation unit 130, which is preferably a conventional cold box, separates the stream 128 into at least a CO-rich stream 132 and an H2 rich stream 131, but can also include minor amounts of one or more residual or tail gas streams of mixed hydrogen, methane and CO used as fuel or exported via line 134. The separation unit 130 can be, for example, a partial condensation box with two columns. The CO-rich stream 132 can be supplied to the acetic acid synthesis unit 136 via line 135, as discussed in more detail below.

The remaining syngas from line 120, CO2 from stream 126, and hydrogen from stream 131, are compressed to methanol synthesis pressure in compressor 138, and fed as makeup stream 123 to the methanol synthesis unit 140 employing a methanol synthesis loop and catalytic methanol synthesis reactors well known in the art. Preferably the SN of the syngas is between 2.0 and 2.1; more preferably between 2.04 and 2.06. Purge gas stream 124 from the synthesis unit 140 is preferably recycled to the CO2 removal unit 122, as described above. As is well known, the purge gas stream 124 is necessary to prevent the buildup of inerts such as argon, nitrogen and methane in the methanol synthesis loop. Processing the purge gas in the CO2 removal unit 122 and the cold box 130 has the advantage of recycling the CO2, CO and hydrogen from the purge gas, while rejecting the inerts to the residual stream 134. Methanol product can be purified by distillation unit 142, or another conventional process. Purified methanol is exported as product via line 144, or a portion may be supplied to the acetic acid synthesis unit 136 via line 145.

The acetic acid synthesis unit 136 employs conventional acetic acid manufacturing equipment and methodology well known and/or commercially available to those skilled in the art to form acetic acid from CO via stream 135 and methanol via stream 145, such as, for example, from one or more of the acetic acid manufacturing patents mentioned above. For example, a conventional BP/Monsanto process can be employed, or an improved BP/Monsanto process employing BP-Cativa technology (iridium catalyst), Celanese low water technology (rhodium-lithium acetate catalyst), Millenium low water technology (rhodium-phosphorous oxide catalyst) and/or dual process methanol carbonylation-methyl formate isomerization. The reaction generally comprises reacting methanol, methyl formate, or a combination thereof in the presence of a reaction mixture comprising carbon monoxide, water, a solvent and a catalyst system comprising at least one halogenated promoter and at least one compound of rhodium, iridium, or a combination thereof. The reaction mixture preferably has a water content up to 20 weight percent. Where the reaction comprises simple carbonylation, the water content in the reaction mixture is preferably from about 14 to about 15 weight percent. Where the reaction comprises low-water carbonylation, the water content in the reaction mixture is preferably from about 2 to about 8 weight percent. Where the reaction comprises methyl formate isomerization or a combination of isomerization and methanol carbonylation, the reaction mixture preferably contains a nonzero quantity of water up to 2 weight percent. The reaction is typically continuous. An acetic acid product is obtained via line 146.

If desired, a portion of the acetic acid from line 146 can be fed via line 147 to an associated process that produces CO2 as a byproduct, such as conventional vinyl acetate monomer (VAM) synthesis unit 148. The acetic acid is reacted with ethylene via line 150 and at least a portion of the oxygen 114 from the air separation unit 116. A liquid product stream 152 is processed in conventional VAM distillation unit 156 to produce essentially pure (commercial specification) VAM via line 158. Carbon dioxide by-product from the VAM synthesis is separated from the reactor effluent gases via conventional CO2 removal system 154 and recycled to the methanol synthesis loop via line 126. The oxygen in line 114 can be obtained, for example, using a conventional (preferably cryogenic) air separation unit 116 producing the amount of oxygen needed to supply both the VAM synthesis unit 148 and the autothermal reformer 118.

VAM production is mainly achieved by the acetoxylation of ethylene according to the reaction:

The main by-product is CO2 formed by the reaction:

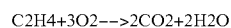

Selectivity for this process yields approximately 7-8% CO2 by mass. A VAM plant producing approximately 100,000 metric tons per year (MTY) requires approximately 35,000 MTY of ethylene and produces between 9,000 and 10,000 MTY of CO2.

Utilities 160, which typically include the steam system, cooling water, compressed air and the like, are supplied within the integrated system as needed, with the further concomitant advantage of economies of scale incidental to larger utility supply systems for the integrated plant relative to each individual unit thereof. Notably, steam generated by waste heat recovery from the steam reformer 109 and ATR 118, as well as from the methanol synthesis unit 140, the acetic acid synthesis unit 136 and/or VAM synthesis unit 148 or any other associated integrated unit, can be used to drive or supply steam to the boiler feed water pump, sweet cooling water pump, sea cooling water pump, natural gas compressor, ASU compressor 115, prereformer 106, ATR 118, $CO_2$ removal unit 122, makeup compressor 138, methanol syngas recycle compressor, and the like, or any combination thereof. In contrast to the typical situation where excess steam is produced by steam reforming, there is preferably no steam exported by the integrated system of the present invention. An auxiliary boiler can supply additional steam as needed.

EXAMPLE 1

In this example, flow rates, compositions and other properties are approximated to two significant figures unless otherwise noted; flow rates are in normal cubic meters per hour (Nm 3/h) and compositions in mole percent, unless otherwise noted. A process according to the embodiment of the invention for a MeOH/AcOH/VAM process shown in FIG. 1 is designed for a plant producing 5016 metric tons per day (MTPD) methanol and 19,400 Nm 3/h CO for acetic acid synthesis. Natural gas 102 is provided at 194,000 Nm 3/h as both fuel 103 for the plant (12,000 Nm 3/h) as well as process feed gas (182,000Nm 3/h). The natural gas has a composition of approximately 89.5% methane, 5.0% ethane, 1.0% propane, 0.5% butane and heavier hydrocarbons, and 4.0% nitrogen, and is supplied to desulfurization unit 104. A first portion of the desulfurized natural gas (127,000 Nm 3/h) is supplied via line 111 with steam (246,000 Nm 3/h) for prereforming 106 and steam reforming 109 to obtain 478,000 Nm 3/h effluent comprising 5.9% $CO_2$, 4.5% CO, 35% hydrogen, 35% steam, 18% methane and less than 2.0% of nitrogen and argon.

The remaining desulfurized natural gas (55,000 Nm 3/h) in line 112 is fed to the autothermal reformer 118 with the steam reformer effluent and 10,000 Nm 3/h recycle $CO_2$ via line 110 comprising 98% $CO_2$ and less than 1% each of CO, hydrogen, water vapor, and methane. The ATR 118 consumes a 115,000 kg/h oxygen stream via line 114 comprising 0.5% argon, and produces 620,000 Nm 3/h of dried effluent comprising 8.0% $CO_2$, 23% CO, 66% hydrogen, 1.8% methane, and less than 1.2% of water vapor, nitrogen and argon.

A 127,000 Nm 3/h portion of the dried effluent from the ATR 118 is-supplied to the $CO_2$ removal unit 122. The $CO_2$-rich stream 110 is described above, and the $CO_2$-lean stream comprises 116,000 Nm 3/h of gas with a composition of 25% CO, 71.6% hydrogen, 2% methane, 1.3% nitrogen and less than 1% of argon, which is supplied to the cold box 130.

The cold box 130 produces a 19,400 Nm 3/h stream 132 comprising 98% CO, 1.7% nitrogen, and less than 1% each of hydrogen, argon and methane, a 65,000 Nm 3/h tail gas stream 134 comprising 11% CO, 84% hydrogen, 2.3% nitrogen, 2.6% methane, and less than 1% argon, and a 32,000 Nm 3/h stream 131 comprising 90% hydrogen, 8.5% CO and less than 1% each of nitrogen, argon and methane.

The remainder of stream 120, along with stream 131, is compressed to stream 123 to supply 527,000 Nm 3/h of makeup gas comprising 68% hydrogen, 22% CO, 7.5% $CO_2$, 1.7% methane, and less than 1.3% each of water vapor, nitrogen and argon (producing a syngas with an R value of 2.04), to the methanol synthesis unit 140. The unit 140 produces the purge gas stream 124 as previously mentioned, 260,000 kg/h of crude methanol containing 24% water, 1.9% $CO_2$, and less than 1% each of CO, hydrogen, argon and methane, and 209,000 kg/h of commercially pure methanol in streams 144 and 145.

Stream 145 supplies 26,000 kg/h of methanol to the acetic acid synthesis unit 136 which is reacted with the CO via stream 135 to obtain 47,600 kg/h of commercial glacial acetic acid after distillation, at a purity greater than 99.85 wt %.

A portion of the acetic acid from line 146 is fed at a rate of 22,000 kg/h to VAM synthesis unit 148 where it is reacted with 10,000 Nm 3/h of polymerization grade ethylene comprising more than 99.9% ethylene, and less than 0.1% impurities, via line 150, and 6,000 Nm 3/h oxygen from air separation unit 116 to obtain 31,000 kg/h of commercial VAM product stream 152, having a purity greater than 99.9 weight percent. VAM production is mainly achieved by the acetoxylation of ethylene. A $CO_2$ stream comprising more than 98% $CO_2$, is produced at 1,400 Nm 3/h is recovered from $CO_2$ removal system 154.

In this example, the $CO_2$ stream produced in the VAM synthesis is not recycled to the methanol synthesis loop via line 126. If necessary or desired, additional $CO_2$ could alternatively or additionally be imported via line 127 to supply the total $CO_2$ needed in line 126.

The steam balance for this exemplary process requires a high-pressure steam auxiliary boiler producing 155 t/h steam at 101 bar and 500° C. The carbon efficiency exclusive of acetic acid synthesis 136 and VAM synthesis 148 (including VAM distillation 156 and $CO_2$ system 154) is approximately 82%.

EXAMPLE 2

Figure 2:
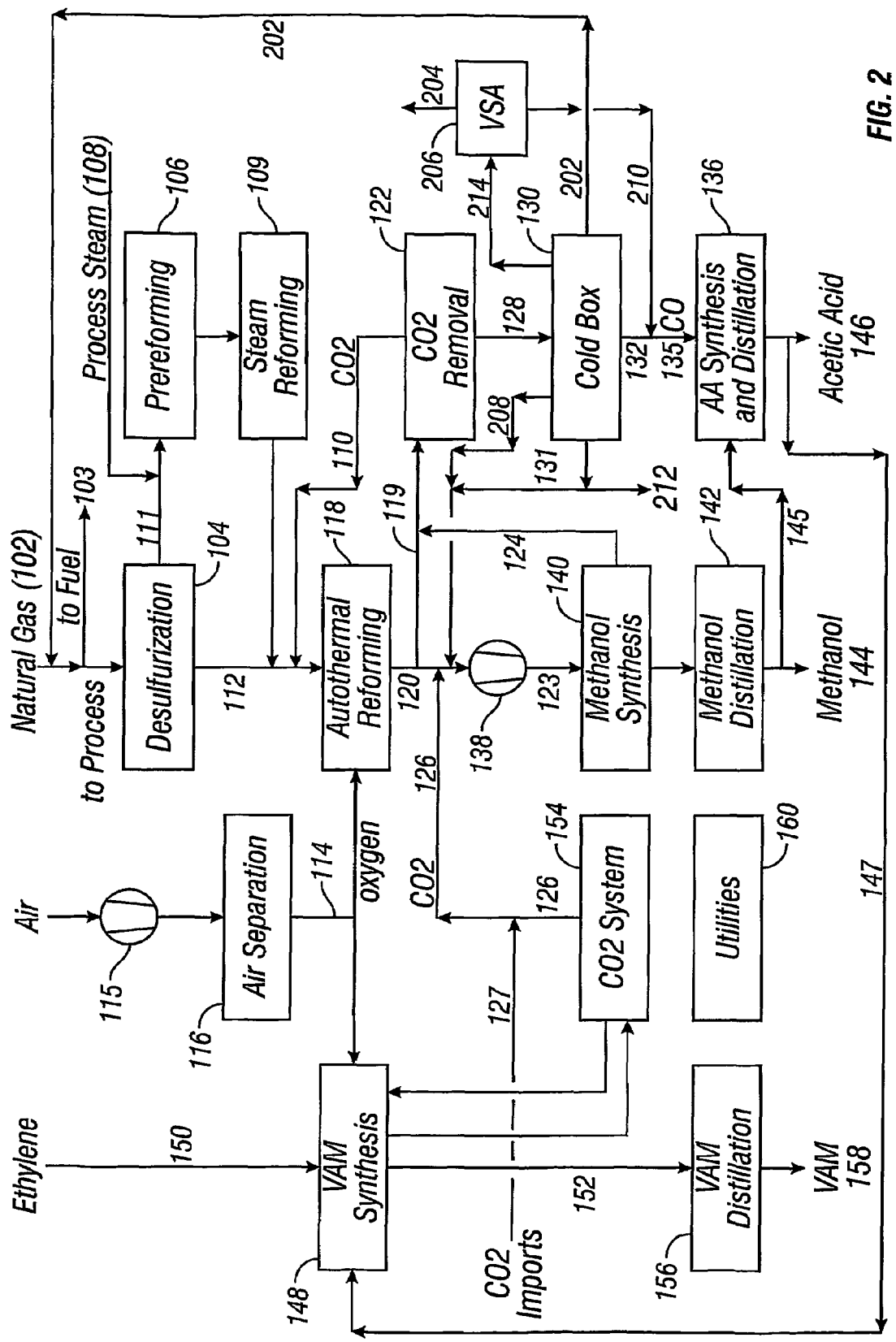
FIG. 2 is a simplified block flow of an embodiment similar to FIG. 1, wherein CO2 emissions are decreased.

In this example, flow rates, compositions and other properties are approximated to two significant figures unless otherwise noted; flow rates are in normal cubic meters per hour (Nm 3/h) and compositions in mole percent, unless otherwise noted. A process according to the embodiment of the invention for a MeOH/AcOH process shown in FIG. 2 is designed for a plant producing 4,400 metric tons per day (MTPD) methanol, 49,000 Nm 3/h CO for acetic acid synthesis and 99,000 Nm 3/h hydrogen for a nearby refinery. Where features found in FIGS. 1 and 2 are identical, the numbers used to identify the feature are identical. Natural gas 102 is provided at 182,000 Nm 3/h as process feed gas. The natural gas has a composition of approximately 89.5% methane, 5.0% ethane, 1.0% propane, 0.5% butane and heavier hydrocarbons, and 4.0% nitrogen, and is supplied to desulfurization unit 104. A first portion of the desulfurized natural gas (127,000 Nm 3/h) is supplied via line 111 with steam 108 (246,000 Nm 3/h) to prereformer 106 and steam reforming 109 to obtain 478,000 Nm 3/h effluent comprising 5.9% $CO_2$, 4.5% CO, 35% hydrogen, 35% steam, 18% methane and less than 2.0% each of nitrogen and argon.

The remaining desulfurized natural gas (55,000 Nm 3/h) from desulfurization unit 104 exits via line 112 and is fed to the autothermal reformer 118, along with the steam reformer effluent and approximately 22,000 Nm 3/h recycle $CO_2$ via line 110 comprising 98% $CO_2$ and less than 1% each of CO, hydrogen, water vapor, and methane. The ATR 118 consumes a 117,000 kg/h oxygen stream via line 114 comprising 0.5% argon, and produces 630,000 Nm 3/h of dried effluent comprising 9.0% CO2, 24% CO, 64% hydrogen, 1.7% methane, and less than 1.3% of water vapor, nitrogen and argon.

A 220,000 Nm 3/h portion of the effluent from the ATR 118, together with the purge stream from methanol synthesis loop 124 is supplied to the CO2 removal unit 122 via 119. The CO2-rich stream 110 is described above, and the CO2-lean stream comprises 235,000 Nm 3/h of gas with a composition of 23% CO, 68% hydrogen, 5% methane, 3% nitrogen and trace amounts of argon, which is supplied to the cold box 130.

In this example, the cold box is based on a methane wash process with three main columns and a small side column to withdraw a nitrogen-rich stream 214. Stream 214 comprises nitrogen and CO in approximately the same proportions. This stream is treated in a VSA (Vacuum Swing Absorber) separation process 206, to recover a useful carbon monoxide-rich stream 210, which is added to CO-rich stream 132 exiting cold box 130, forming stream 135. VSA 206 also produces nitrogen stream 204. Cold box 130 produces a 44,000 Nm 3/h stream 132 of 98% CO with 1.3% nitrogen and less than 1% hydrogen, argon and methane; a tail gas stream 202 of 9,200 Nm 3/h comprising more than 98% methane and less than 2% of impurities; an 8,300 Nm 3/h flash gas stream 208 comprising 59% hydrogen, 36% carbon monoxide, 3% methane and 1% nitrogen; and a 144,000 Nm 3/h stream 131 comprising 98.5% hydrogen, 1% methane and less than 0.5% each of nitrogen and argon. Tail gas stream 202 can be supplied as feed with natural gas 102. A portion of hydrogen-rich stream 131 may be separated in stream 212 and used in an associated process, such as in a refinery.

The remainder of stream 120 along with the flash gas stream 208 and a portion of stream 131, is compressed to stream 123 to supply 460,000 Nm 3/h of makeup gas comprising 68% hydrogen, 22% CO, 7.5% CO2, 1.6% methane, and less than 1.2% each of water vapor, nitrogen and argon (R=2.03), to the methanol synthesis unit 140. The unit 140 produces purge gas stream 124 as previously mentioned, 228,000 kg/h of crude methanol containing 24% water, 1.9% CO2, and less than 1% each of CO, hydrogen, argon and methane, and 183,000 kg/h of commercially pure methanol in streams 144 and 145.

Stream 145 supplies 65,000 kg/h of methanol to acetic acid synthesis unit 136, where it is reacted with CO via stream 135 to obtain 120,000 kg/h of glacial acetic acid, at a purity greater than 99.85 weight percent after distillation.

A portion of the acetic acid product 146 is fed via 147 to VAM synthesis unit 148 where it is reacted with 10,000 Nm 3/h of polymerization grade ethylene comprising more than 99.9% ethylene, and less than 0.1% of impurities, via line 150, and 6,000 Nm 3/h oxygen from air separation unit 116 to obtain 31,000 kg/h of commercial VAM product stream 152, with a purity greater than 99.9 wt %. VAM production is mainly achieved by the acetoxylation of ethylene. A CO2 stream comprising more than 98% CO2, is produced at 1,400 Nm 3/h is recovered from CO2 removal system 154.

In this example, CO2 from the VAM synthesis is not recycled to the methanol synthesis loop via line 126. If necessary or desired, additional CO2 may be imported via line 127 to supply the total CO2 needed in line 126. In this example, the integrated methanol acetic acid plant produces methanol and acetic acid and supplies 99,000 Nm 3/h of hydrogen for a nearby refinery.

The major portion of high nitrogen content of natural gas is purged in the VSA, along with a small quantity of CO. The additional fuel gas requirements for the fired preheater and reformer, as well as for the required boiler, could be advantageously fulfilled by the extra hydrogen, resulting in an integrated complex with very low CO2 emissions (less than 2,500 Nm 3/h or less than 10% of the carbon input), if hydrogen cannot be used elsewhere.

The invention claimed is:

1. A method for manufacturing methanol and acetic acid, characterized by the integrated steps of:
   separating a hydrocarbon source into first and second hydrocarbon streams;
   steam reforming the first hydrocarbon stream with steam to produce a reformed stream;
   autothermal reforming of a mixture of the reformed stream and the second hydrocarbon stream with oxygen and carbon dioxide to produce a syngas stream;
   separating a minor portion of the syngas stream into a carbon dioxide-rich stream, a hydrogen-rich stream, and a carbon monoxide-rich stream;
   recycling the carbon dioxide-rich stream to the autothermal reforming;
   compressing a remaining portion of the syngas stream, at least a portion of the hydrogen-rich stream to supply a makeup stream to a methanol synthesis loop to obtain a methanol product; and
   synthesizing acetic acid from at least a portion of the methanol product and the carbon monoxide-rich stream.

2. The method of claim 1, wherein the makeup stream has a stoichiometric number (SN) between 2.0 and 2.1, wherein the SN is calculated from component concentrations as $[(H_2-CO_2)/(CO+CO_2)]$.

3. The method of any one of the preceding claims, further comprising supplying a purge gas stream from the methanol synthesis loop to the step of separating the minor portion of the syngas stream into a carbon dioxide-rich stream, a hydrogen-rich stream, and a carbon monoxide-rich stream.

4. The method of claims 1, wherein the autothermal reformer is a single train autothermal reformer.

5. The method of claims 1, wherein the step of separating the minor portion of the syngas stream into a carbon dioxide-rich stream, a hydrogen-rich stream, and a carbon monoxide-rich stream, includes supplying the minor portion of the syngas to a methane wash cold box unit.

6. The method of claim 5, wherein a flash gas from the step of separating the minor portion of the syngas stream into a carbon dioxide-rich stream, a hydrogen-rich stream, and a carbon monoxide-rich stream, is recycled to the methanol synthesis loop.

7. The method of any one of claims 5 or 6, wherein a tail gas stream from the cold box is recycled as feed gas.

8. The method of claim 1, wherein carbon dioxide emissions are less than 10% of the total carbon input.

9. The method of claim 1, wherein carbon dioxide emissions are less than 5 percent of the total carbon input.

10. The method of claim 1, wherein a first portion of the hydrogen-rich stream from the separation step is recycled to the methanol synthesis loop and a second portion is sent as feed to an associated process.

11. The method of claim 1, further comprising supplying a carbon dioxide stream from an associated process to supply the makeup stream.

12. The method of any one of claims 10 or 11, wherein the associated process uses the acetic acid as a reactant, uses the methanol product as a reactant, shares oxygen from a common air separation unit, shares common utilities, or a combination thereof.

13. The method of claim 12, further comprising:
   providing at least a portion of the acetic acid produced to a vinyl acetate monomer synthesis loop in the associated process;

combining the portion of the acetic acid with an ethylene source and oxygen to produce vinyl acetate monomer.

14. The method of claim 13, wherein a single air separation unit supplies oxygen to the associated process and the autothermal reformer.

15. The method of claim 1, wherein at least 10% of the syngas stream is directed to the step of separating the minor portion of the syngas stream into a carbon dioxide-rich stream, a hydrogen-rich stream, and a carbon monoxide-rich stream.

16. The method of claim 1, wherein the methanol produced is between 1,000 and 30,000 tons/day.

17. The method of claim 1, wherein the acetic acid produced is between 500 and 6,000 metric tons/day.

18. The method of claim 1, further comprising importing a CO2-rich stream to the methanol synthesis loop.

19. The method of claim 13, further comprising importing a CO2-rich stream from the vinyl acetate monomer synthesis loop to the methanol synthesis loop.

20. The method of claim 18, wherein the hydrocarbon source comprises natural gas and a ratio of the imported CO2 stream to the hydrocarbon source is at least 0.05 kg CO2 per Nm3 natural gas.

21. The method of claim 20, wherein the ratio of the imported CO2 stream to the natural gas is at least 0.2 kg CO2 per Nm3 natural gas.

22. The method of claim 19, wherein the ratio of the imported CO2 to the natural gas is at least 0.23 kg CO2 per Nm3 natural gas.

23. The method of any claim 1, comprising:
diverting between 35 and 65% of the feed gas stream to the first stream; and
diverting between 35 and 65% of the feed gas stream to the second stream.

24. The method of any claim 1, comprising:
diverting 45 to 55% of the feed gas stream to the first stream; and
diverting 45 to 55% of the feed gas stream to the second stream.

25. The method of claim 1 wherein the step of separating the minor portion of the syngas stream into a carbon dioxide-rich stream, a hydrogen-rich stream, and a carbon monoxide-rich stream, produces a tail gas stream enriched in inerts.

* * * * *